United States Patent
Nagamori et al.

(10) Patent No.: US 10,115,992 B2
(45) Date of Patent: Oct. 30, 2018

(54) ELECTRODE CATALYST, GAS DIFFUSION ELECTRODE-FORMING COMPOSITION, GAS DIFFUSION ELECTRODE, MEMBRANE ELECTRODE ASSEMBLY, AND FUEL CELL STACK

(71) Applicant: N.E. CHEMCAT Corporation, Tokyo (JP)

(72) Inventors: Kiyotaka Nagamori, Bando (JP); Tomoteru Mizusaki, Bando (JP); Yoko Nakamura, Bando (JP); Hiroshi Igarashi, Bando (JP); Yasuhiro Seki, Bando (JP)

(73) Assignee: N.E. Chemcat Corporation, Tokyo (JP)

( * ) Notice: Subject to any disclaimer, the term of this patent is extended or adjusted under 35 U.S.C. 154(b) by 0 days.

(21) Appl. No.: 15/648,063

(22) Filed: Jul. 12, 2017

(65) Prior Publication Data
US 2017/0331135 A1   Nov. 16, 2017

Related U.S. Application Data

(63) Continuation of application No. 15/542,367, filed as application No. PCT/JP2016/076280 on Sep. 7, 2016.

(30) Foreign Application Priority Data
Sep. 18, 2015   (JP) .................................. 2015-185974

(51) Int. Cl.
*H01M 8/1004* (2016.01)
*H01M 4/86* (2006.01)
(Continued)

(52) U.S. Cl.
CPC ........... *H01M 8/1004* (2013.01); *H01M 4/86* (2013.01); *H01M 4/9075* (2013.01); *H01M 4/92* (2013.01)

(58) Field of Classification Search
CPC .... H01M 8/1004; H01M 4/86; H01M 4/9075; H01M 4/92
See application file for complete search history.

(56) References Cited

U.S. PATENT DOCUMENTS

2003/0079566 A1   5/2003   Biberbach
2006/0042957 A1   3/2006   He
(Continued)

FOREIGN PATENT DOCUMENTS

CA   2911438 A1   11/2014
EP   2995378 A1   3/2016
(Continued)

OTHER PUBLICATIONS

Office Action dated Nov. 1, 2017 from the Korean Intellectual Property Office regarding the corresponding Korean patent application No. 10-2017-7018276.
(Continued)

*Primary Examiner* — Jane J Rhee
(74) *Attorney, Agent, or Firm* — Troutman Sanders LLP

(57) ABSTRACT

Provided is an electrode catalyst in which the contents of chlorine (Cl) species and bromine (Br) species are reduced to a predetermined level or lower, capable of exhibiting sufficient catalyst performance. The electrode catalyst has a core-shell structure including a support, a core part formed on the support and a shell part formed to cover at least a part of the surface of the core part. A concentration of bromine (Br) species of the electrode catalyst as measured by X-ray fluorescence (XRF) spectroscopy is 400 ppm or less, and a concentration of chlorine (Cl) species of the electrode catalyst as measured by X-ray fluorescence (XRF) spectroscopy is 900 ppm or less.

14 Claims, 4 Drawing Sheets

(51) Int. Cl.
*H01M 4/90* (2006.01)
*H01M 4/92* (2006.01)

(56) References Cited

U.S. PATENT DOCUMENTS

| | | |
|---|---|---|
| 2010/0197490 A1 | 8/2010 | Adzic et al. |
| 2014/0171290 A1 | 6/2014 | Lopez |
| 2016/0126560 A1 | 5/2016 | Maruyama |
| 2016/0233517 A1 | 8/2016 | Nagamori et al. |
| 2017/0331118 A1 | 11/2017 | Nagamori et al. |

FOREIGN PATENT DOCUMENTS

| | | |
|---|---|---|
| EP | 3035425 A1 | 6/2016 |
| JP | S52-041738 A | 3/1977 |
| JP | 2002 249488 A | 9/2002 |
| JP | 2002249488 A | 9/2002 |
| JP | 2003129102 A | 8/2003 |
| JP | 2008511534 A | 4/2008 |
| JP | 2008126211 A | 6/2008 |
| JP | 2009043457 A | 2/2009 |
| JP | 2009 114545 A | 5/2009 |
| JP | 2009114545 A | 5/2009 |
| JP | 004286499 B2 | 7/2009 |
| JP | 2009238560 A | 10/2009 |
| JP | 2010140465 A | 6/2010 |
| JP | 2010214330 A | 9/2010 |
| JP | 2011-3492 A | 1/2011 |
| JP | 2011003492 A | 1/2011 |
| JP | 2011212666 A | 10/2011 |
| JP | 2011218278 A | 11/2011 |
| JP | 2014239033 A | 12/2014 |
| JP | 2015140465 A | 8/2015 |
| JP | S58-46670 B2 | 1/2016 |
| KR | 2003-0012824 A | 2/2003 |
| KR | 2010-0003780 A | 1/2010 |
| WO | 2006026144 A1 | 3/2006 |
| WO | 2011115012 A1 | 9/2011 |
| WO | 2014/181873 A1 | 11/2014 |
| WO | 2014181873 A1 | 11/2014 |
| WO | 2015147308 A1 | 10/2015 |

OTHER PUBLICATIONS

Extended European Search Report dated Dec. 1, 2017 during the prosecution of European Patent Application No. 16846336.2.
Notification of Reasons for Refusal (Japanese Office Action) dated Feb. 21, 2017, filed in Japanese Patent Application No. 2016-174335.
Office action dated Jun. 21, 2017 during the prosecution of corresponding European patent application No. 15768953.0.
Office action dated Aug. 10, 2017 during the prosecution of corresponding Canadian patent application No. 2,924,306.
Matsuoka et al., "Degradation of Polymer Electrolyte Fuel Cells under the Existence of Anion Species", J. Power Sources, May 1, 2008, vol. 179 No. 2, p. 560-565.
Canadian Office Action dated Jul. 4, 2016 issued in corresponding Canadian Patent Application No. 2,924,306.
Extended European Search Report dated Aug. 25, 2016 issued in corresponding European Patent Application No. 15768953.0.
Zhang, et al., "Pd@Pt Core-Shell Nanostructures with Controllable Composition Synthesized by a Microwave Method and Their Enhanced Electrocatalytic Activity toward Oxygen Reduction and Methanol Oxidation", J. Phys. Chem. C, 2010, 114 (27), pp. 11861-11867.
Simone, et al., "Reversible Poisoning of Palladium Catalysts for Methane Oxidation Article in Applied Catalysis", 70 (1):87-100, Dec. 1991.
Korean Office Action dated Jul. 15, 2016 issued in corresponding Korean Patent Application No. 2016-7007187.
PCT International Search Report dated Jun. 23, 2015 issued in corresponding PCT International Application No. PCT/JP2015/059810.
International Search Report dated Nov. 24, 2016, filed in PCT/JP2016/076280.

ELECTRODE CATALYST, GAS DIFFUSION ELECTRODE-FORMING COMPOSITION, GAS DIFFUSION ELECTRODE, MEMBRANE ELECTRODE ASSEMBLY, AND FUEL CELL STACK

CROSS-REFERENCE TO RELATED APPLICATIONS

This application is continuation of U.S. patent application Ser. No. 15/542,367, filed Jul. 7, 2017, which is a U.S. national phase application under 35 U.S.C. § 371 of International Patent Application No. PCT/JP2016/076280, filed on Sep. 7, 2016, and claims benefit of priority to Japanese Patent Application No. 2015-185974, filed Sep. 18, 2015. The entire contents of these applications are hereby incorporated by reference.

TECHNICAL FIELD

This invention relates to an electrode catalyst. Also, this invention relates to a composition for forming a gas diffusion electrode, a gas diffusion electrode, a membrane-electrode assembly, and a fuel cell stack that include the electrode catalyst.

BACKGROUND

A so-called polymer electrolyte fuel cell (Polymer Electrolyte Fuel Cell: hereinafter called "PEFC" as needed), has its operating temperature of from a room temperature to about 80° C. Also, since PEFC makes it possible to employ inexpensive general-purpose plastics, etc. for members constituting its fuel cell body, it is possible to realize reduction in weight. Furthermore, PEFC makes it possible to achieve thinning of a polymer electrolyte membrane, enabling an electric resistance to be reduced, thereby enabling a power loss to be reduced relatively easily. Due to PEFC having not a few advantages as described above, it is applicable to a fuel cell vehicle, a home cogeneration system, and the like.

As an electrode catalyst for PEFC, there has been proposed an electrode catalyst in which platinum (Pt) or a platinum (Pt) alloy, i.e., a component for the electrode catalyst, is supported on a carbon serving as a support (for example, Japanese Patent Application Publication No. 2011-3492, MATSUOKA et al., "Degradation of Polymer Electrolyte fuel cells under the existence of anion species", J. Power Sources, 2008 May 1, Vol. 179 No. 2, P.560-565).

Conventionally, there have been disclosed that, as for an electrode catalyst for PEFC, if the content of chlorine contained in the electrode catalyst is 100 ppm or more, it is not desirable as an electrode catalyst (for example, Japanese Patent No. 4,286,499); and that this is because if the content of chlorine contained in the electrode catalyst is 100 ppm or more, it is impossible to obtain a sufficient catalytic activity for the electrode catalyst for fuel cells; and corrosion of its catalyst layer will occur, thus shortening the life of the fuel cell.

Then, there is disclosed, as the catalyst component of the electrode catalyst, a powder of platinum (Pt) or platinum (Pt) alloy that contains less than 100 ppm of chlorine (for example, Japanese Patent No. 4,286,499).

As for the preparation of the powder of platinum (Pt) or platinum (Pt) alloy, there is disclosed the following method: forming a melt which contains, as starting materials, a chlorine-free platinum compound and a chlorine-free compound of alloying elements; heating the melt up to a reaction temperature at which the platinum compound and the compound of the alloying elements are thermally decomposed to give an oxide; cooling the melt; and the melt is dissolved in water and the resulting oxide or mixed oxides are converted into a powder of platinum or platinum alloy by successive reduction.

Further, there is disclosed a PEFC in which part of protons of an acid group of an electrolyte contained in a catalyst layer of an electrode of a membrane-electrode assembly is exchanged for a phosphonium ion, defining a compound structure such that a counter anion of the phosphonium contains no halogen elements (for example, Japanese Patent No. 5,358,997). The reason, as is disclosed therein, is that residues of the halogen elements in the electrode cause a degradation in cell performance. Specifically, it is described that the residues of a fluoride ion, a chloride ion, or a bromide ion amongst halide ions in the electrode sometimes cause degradation in cell performance, and particularly, the residues of the chloride ion in the electrode poison the electrode catalyst, and cause Pt serving as a catalyst to be eluted from a catalyst layer as a complex ion such as $PtCl_4^{2-}$, $PtCl_6^{2-}$ to cause degradation of the cell performance.

Moreover, there is disclosed a method for producing core-shell particles obtained by filtering a dispersion liquid having core-shell particles dispersed in a solvent using ultrafilters or the like, cleaning and substituting the same with a solvent as necessary (for example, Japanese Patent No. 5,443,029). Specifically, there is disclosed in a preparation process of a core metal particles dispersion liquid, the core metal particles dispersion liquid was cleaned until no Cl ions were detected.

Further, there is disclosed a method for producing carbon supported core-shell catalyst fine particles which controls a deposition of a shell metal material composing a shell part on a surface of a carbon support (for example, Japanese Patent No. 5,672,752). Furthermore, there is disclosed a method for producing a platinum core-shell catalyst capable of directly depositing platinum on a gold core particle (for example, Japanese Patent No. 5,660,603). In production processes provided in these two methods for producing a electrode catalyst (core-shell catalyst), it is disclosed that the electrode catalyst (core-shell catalyst) is cleaned with extra pure water.

However, the methods for producing an electrode catalyst (core-shell catalyst) disclosed in the aforementioned patent documents focus on chlorine only amongst halogens, and merely work on reduction/removal of chlorine although it shows the findings that residues of halogens reduce cell performance.

The applicant of the present patent application presents the following publications as those that describe the aforementioned inventions known to the public through publications.

SUMMARY

As mentioned above, from the viewpoint of improving catalytic activity and lifetime as an electrode catalyst for PEFC, it is important to reduce the content of halogen, particularly of chlorine species contained in the catalyst.

However, the present inventors have found out that when a core-shell catalyst is employed as an electrode catalyst for PEFC, a sufficient catalyst performance cannot be obtained unless not only the content of chlorine species but the content of bromine species is reduced to a predetermined level or lower, and that bromine species has a greater impact than chlorine species on degradation of catalyst performance. Namely, in a case where a core-shell catalyst is employed as an electrode catalyst for PEFC, there has been room for improvement in the aforementioned conventional techniques.

This invention has been made in view of such technical circumstances, and it is an object of this invention to provide an electrode catalyst having the contents of chlorine species and bromine species reduced to predetermined levels or lower, enabling the electrode catalyst to exhibit sufficient catalytic performance.

Further, it is another object of this invention to provide a composition for forming a gas diffusion electrode, a gas diffusion electrode, a membrane-electrode assembly (MEA), and a fuel cell stack that include the aforementioned electrode catalyst.

The present inventors, as a result of having performed intensive studies, found out that it is possible to constitute an electrode catalyst which exhibits a satisfactory catalyst performance (a core-shell catalyst to be described later) by reducing the concentration of chlorine (Cl) species contained in the electrode catalyst to 900 ppm or lower and by reducing the concentration of bromine (Br) species contained therein to 400 ppm or lower, when measured by X-ray fluorescence (XRF), and have completed this invention.

More specifically, this invention includes the following technical matters:

That is, this invention provides:

(1) an electrode catalyst having a core-shell structure including:
a support;
a core part formed on the support; and
a shell part formed to cover at least a part of a surface of the core part,
wherein the concentration of bromine (Br) species is not higher than 400 ppm when measured by X-ray fluorescence (XRF) spectroscopy, and the concentration of chlorine (Cl) species is not higher than 900 ppm when measured by X-ray fluorescence (XRF) spectroscopy.

Since the concentrations of chlorine (Cl) species and bromine (Br) species contained in the catalyst are respectively rendered to be not greater than 900 ppm and not greater than 400 ppm, the electrode catalyst of this invention can exhibit a sufficient catalytic activity as an electrode catalyst.

Further, the electrode catalyst has a core-shell structure, and is suitable for reducing the manufacturing cost.

In this invention, the bromine (Br) species refers to a chemical species containing bromine as a constituent element. Specifically, the chemical species containing bromine include bromine atom (Br), bromine molecule ($Br_2$), bromide ion ($Br^-$), bromine radical (Br.), polyatomic bromine ion and a bromine compound (e.g. X—Br where X represents a counterion).

In this invention, the chlorine (Cl) species refers to a chemical species containing chlorine as a constituent element. Specifically, the chemical species containing chlorine include chlorine atom (Cl), chlorine molecule ($Cl_2$), chloride ion ($Cl^-$), chlorine radical (Cl.), polyatomic chloride ion and a chlorine compound (e.g. X—Cl where X represents a counterion).

In this invention, bromine (Br) species concentration and chlorine (Cl) species concentration are measured by X-ray fluorescence (XRF) spectrometry. A value of the bromine (Br) species contained in the electrode catalyst that is measured by X-ray fluorescence (XRF) spectrometry is the concentration of bromine (Br) species. Likewise, A value of the chlorine (Cl) species contained in the electrode catalyst that is measured by X-ray fluorescence (XRF) spectrometry is the concentration of chlorine (Cl) species.

Here, the bromine (Br) species concentration and chlorine (Cl) species concentration are concentrations of the bromine atoms and chlorine atoms in terms of the bromine element and chlorine element that are respectively contained in the electrode catalyst.

As stated above, with respect to the core-shell catalyst, the present inventors also focused on bromine (Br) species other than chlorine (Cl) species, and found out that it is important to sufficiently remove them as impurities.

Bromine being a halogen element as with chlorine, is an element from the same family (7B) as chlorine, and they have analogous physical properties as represented by e.g., their ion radii. For this reason, a bromine-containing metal compound is sometimes used as a raw material for the core part or shell part of a core-shell catalyst, instead of a chloride salt of palladium (Pd) and platinum (Pt). Further, the bromine-containing metal compound is sometimes used as a precursor for producing the chloride salt of platinum (Pt) that is employed as a raw material of the core-shell catalyst. Moreover, during a production process, the bromine (Br) species is sometimes unintentionally mixed with the core-shell catalyst, adhering to the electrode catalyst as an impurity.

Further, the present inventors found out that the bromine (Br) species has a greater impact on the degradation of catalyst performance, than the chloride (Cl) species. From this viewpoint, in the electrode catalyst of this invention as set forth in (1), (2) the bromine (Br) species concentration is preferably not greater than 300 ppm, and (3) the bromine (Br) species concentration is more preferably not greater than 200 ppm.

Thus can be achieved the effects of this invention more reliably.

Further, from the viewpoint of more reliably achieving the effects of this invention, it is preferable to reduce as much chlorine (Cl) species as possible, specifically, (4) the chlorine (Cl) species concentration is preferably less than 900 ppm, more preferably not greater than 800 ppm, and still more preferably not greater than 600 ppm.

Further, in this invention, (5) the chlorine (Cl) species concentration may be equal to or higher than 0 ppm. Here, in this invention, "the chlorine (Cl) species concentration is 0 ppm" denotes a state in which the chloride (Cl) species measured through X-ray fluorescence (XRF) spectroscopy, is reduced to a level at which the chloride (Cl) species is not detected (undetected). Although it is ideal that the chlorine (Cl) species is thoroughly removed in order to improve the catalyst performance, the present inventors confirmed that the catalyst performance sufficiently improves by reducing the chloride (Cl) species to a level at which the chloride (Cl) species measured through X-ray fluorescence (XRF) spectroscopy, is not detected (undetected). In the case of this invention, the detection limit of the chlorine (Cl) species measured through X-ray fluorescence (XRF) spectroscopy, is 100 ppm. Consequently, in the case that "the chlorine (Cl) species concentration is 0 ppm", there is a possibility that the chlorine (Cl) species may be contained in a concentration range of less than 100 ppm.

Further, the bromine (Br) species concentration may be equal to or higher than 0 ppm. Similarly, with regard to the bromine (Br) species concentration, "the bromine (Br) species concentration is 0 ppm" denotes a state in which the bromine (Br) species measured through X-ray fluorescence (XRF) spectroscopy, is reduced to a level at which the bromine (Br) species is not detected (undetected). As to this bromine (Br) species concentration as well, the present inventors confirmed that the catalyst performance has sufficiently improved by reducing the bromine (br) species to a level at which the bromine (Br) species measured through X-ray fluorescence (XRF) spectroscopy, is not detected (undetected). In the case of this invention, the detection limit of the bromine (Br) species measured through X-ray fluorescence (XRF) spectroscopy, is 100 ppm. Consequently, in the case that "the bromine (Br) species concentration is 0 ppm", there is a possibility that the bromine (Br) species may be contained in a concentration range of less than 100 ppm.

Further, in the electrode catalysts (1) to (5) of this invention, if the bromine (Br) species and the chlorine (Cl) species concentrations have been respectively reduced to not greater than 400 ppm and not greater than 900 ppm, (6) the chlorine (Cl) species concentration may be not less than 100 ppm. Namely, the chlorine (Cl) species concentration may be from 100 ppm to 900 ppm.

In this case as well, the effects of this invention can be attained. According to this structure, the chlorine (Cl) species concentration is not reduced to less than 100 ppm, thus making it possible to reduce costs and labors for reducing the chlorine in the production process.

Further, this invention provides (7) the electrode catalyst set forth in any one of (1) to (6), wherein the core-shell structure includes: the core part; and a single-layered shell part having the shell part formed to cover at least a part of the surface of the core part.

In this case as well, the effects of this invention can be attained. By employing the aforementioned structure, the electrode catalyst of this invention may reduce the content of a noble metal (s) such as platinum used in the core part, thereby enabling reduction in raw material cost.

According to the structure of the invention (7), namely, (8) in a case of the shell part being of the single-layered structure, it is preferable that the shell part contain at least one metal selected from platinum (Pt) and a platinum (Pt) alloy. This makes it possible to more easily obtain a superior catalytic activity.

Further, according to the structure of the invention (8), namely, (9) in a case of the shell part being of the single-layered structure, it is preferable that the core part contain at least one kind of metal selected from the group consisting of palladium (Pd), a palladium (Pd) alloy, a platinum (Pt) alloy, gold (Au), nickel (Ni) and a nickel (Ni) alloy. This makes it possible to more reliably obtain the effects of this invention. Furthermore, by employing the aforementioned structure, a higher catalyst activity and a higher durability can be obtained.

Further, when this invention has the structure (8), namely,

(10) in a case of the shell part being of the single-layered structure, the core part may contain one or more metal elements other than noble metals as a main component(s). In this structure as well, the effects of this invention can be attained. Furthermore, by employing this structure, cost reduction can be easily achieved due to reduction in noble metal content.

Further, this invention provides the electrode catalyst as set forth in any one of (7) to (9), in which,

(11) in a case of the shell part being of the single-layered structure, the support contains an electrically conductive carbon, the shell part contains platinum (Pt), and the core part contains palladium (Pd).

Thus, the effects of this invention can be achieved more reliably. Further, by employing the abovementioned structure, there can be achieved a higher catalytic activity and a higher durability. Furthermore, by employing the abovementioned structure, the electrode catalyst of this invention, as compared to conventional electrode catalysts having a structure where platinum is supported on a carbon support, is capable of reducing the amount of platinum contained, and is thus capable of easily reducing a raw material cost.

Furthermore, according to this invention,

(12) there is provided the electrode catalyst as set forth in any one of (1) to (6),
in which the core-shell structure has:
the core part; and
a two-layered shell part having a first and a second shell parts formed such that the first shell part covers at least a part of the surface of the core part, and the second shell part covers at least a part of a surface of the first shell part.

Thus, the effects of this invention can be achieved more reliably. By employing the abovementioned structure, the electrode catalyst of this invention may reduce the contained amount of a noble metal(s) such as platinum used in the core part, and is thus capable of easily reducing a raw material cost.

When this invention employs the structure of the invention (12), namely,

(13) in a case of the shell part being of the two-layered structure, it is preferable that the second shell part contain at least one metal selected from platinum (Pt) and a platinum (Pt) alloy. This makes it possible to more easily obtain a superior catalytic activity.

Further, when this invention employs the structure of the invention (13), namely,

(14) in a case of the shell part being of the two-layered structure, it is preferable that the first shell part contain at least one kind of metal selected from the group consisting of palladium (Pd), a palladium (Pd) alloy, a platinum (Pt) alloy, gold (Au), nickel (Ni) and a nickel (Ni) alloy. In this way, the effects of this invention can be achieved more reliably. Furthermore, employing the aforementioned structure makes it possible to obtain a higher catalytic activity and a higher durability.

Further, when this invention has the structure (14), namely,

(15) in a case of the shell part being of the two-layered structure, it is preferable that the core part contain one or more metal elements other than noble metals as a main component(s). In this structure as well, the effects of this invention can be attained. Furthermore, by employing this structure, cost reduction can be more easily achieved due to reduction in noble metal content.

Also, this invention provides the electrode catalyst as set forth in (13) to (15) in which

(16) in a case of the shell part being of the two-layered structure, the first shell part contains palladium (Pd), and the second shell part contains platinum (Pt).

In this way, the effects of this invention can be achieved more reliably. By employing the abovementioned structure, there can be achieved a higher catalytic activity and a higher durability.

Further, this invention provides

(17) a composition for forming a gas diffusion electrode, including the electrode catalyst as set forth in any one of (1) to (16).

According to the gas diffusion electrode-forming composition of this invention, it is possible to easily produce a gas diffusion electrode with a high catalytic activity (polarization property) because it contains the electrode catalyst of this invention.

Furthermore, this invention provides

(18) a gas diffusion electrode containing the electrode catalyst as set forth in any one of (1) to (16).

According to the gas diffusion electrode of this invention, it is possible to achieve a high catalytic activity (polarization property) because it contains the electrode catalyst of this invention.

Furthermore, this invention provides

(19) a membrane-electrode assembly (MEA) including the gas diffusion electrode as set forth in (18).

According to the membrane-electrode assembly (MEA) of this invention, it is possible to achieve a high battery property because it contains the gas diffusion electrode of this invention.

Still further, this invention provides

(20) a fuel cell stack including the membrane-electrode assembly (MEA) as set forth in (19).

According to the fuel cell stack of this invention, it is possible to achieve a high battery property because it contains the membrane-electrode assembly (MEA) of this invention.

According to this invention, there can be provided an electrode catalyst that can exhibit a sufficient catalytic activity, because the concentrations of chlorine (Cl) species and bromine (Br) species contained in the electrode catalyst are respectively rendered to be not greater than 900 ppm (preferably less than 900 ppm) and not greater than 400 ppm (preferably not greater than 300 ppm, more preferably not greater than 200 ppm).

Further, according to this invention, there can be provided an electrode catalyst that is also suitable for reduction of the manufacturing cost because the electrode catalyst has the core-shell structure.

Further, according to this invention, there can be provided a composition for forming a gas diffusion electrode, a gas diffusion electrode, a membrane-electrode assembly (MEA), and a fuel cell stack that include the aforementioned electrode catalyst.

DETAILED DESCRIPTION

Examples of this invention are described in detail hereunder with reference to the drawings when necessary.

Figure 1:
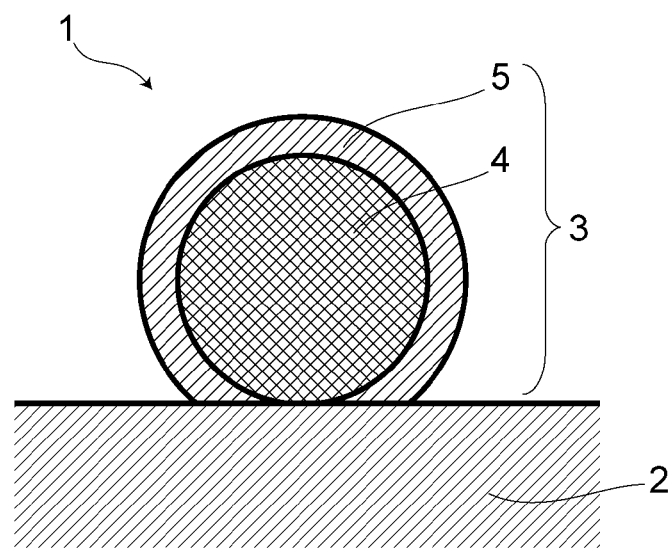
FIG. 1 is a schematic sectional view showing an example of the electrode catalyst (core-shell catalyst) of this invention.

FIG. 1 is a schematic cross-sectional view showing a preferable embodiment of an electrode catalyst (core-shell catalyst) of this invention.

As shown in FIG. 1, an electrode catalyst 1 of this invention includes a support 2; and catalyst particles 3 supported on the support 2 and having a so-called "core-shell structure." Each catalyst particle 3 has a core part 4; and a shell part 5 covering at least a part of the surface of the core part 4. The catalyst particles 3 thus have a so-called "core-shell structure" including the core part 4 and the shell part 5 formed on the core part 4.

That is, the electrode catalyst 1 has the catalyst particles 3 supported on the support 2, and the catalyst particles 3 have the structure where the core part 4 serves as a core (core portion), and the shell part 5 as a shell covers at least a part of the surface of the core part 4.

Further, the constituent element (chemical composition) of the core part 4 and the constituent element (chemical composition) of the shell part 5 differ from each other in composition.

There are no particular restrictions on the electrode catalyst 1 of this invention except that the shell part 5 has to be formed on at least a part of the surface of the core part 4 of each catalyst particle 3.

For example, in terms of more reliably achieving the effects of this invention, it is preferred that the electrode catalyst 1 be in a state where the whole range of the surface of the core part 4 is substantially covered by the shell part 5, as shown in FIG. 1.

Further, the electrode catalyst 1 may also be in a state where a part of the surface of the core part 4 is covered by the shell part 5, and the rest part of the surface of the core part 4 is thus partially exposed, provided that the effects of this invention can be achieved.

That is, with regard to the electrode catalyst of this invention, it is sufficient that the shell part be formed on at least a part of the surface of the core part.

Figure 2:
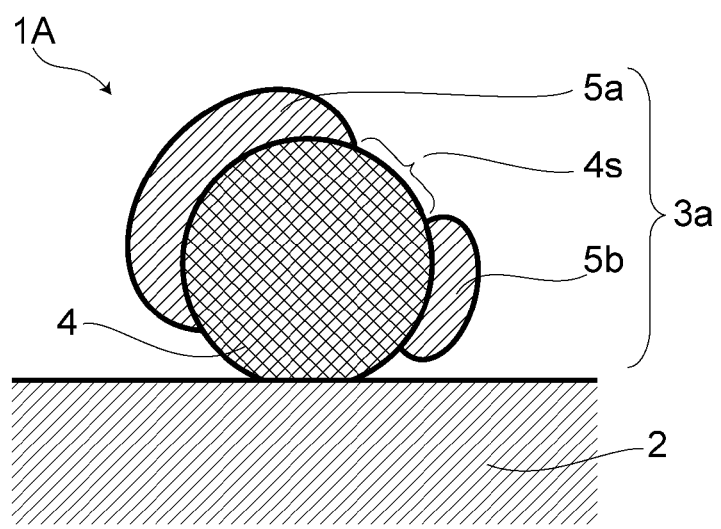
FIG. 2 is a schematic sectional view showing another example of the electrode catalyst (core-shell catalyst) of this invention.

FIG. 2 is a schematic cross-sectional view showing another preferable embodiment (electrode catalyst 1A) of the electrode catalyst (core-shell catalyst) of this invention.

As shown in FIG. 2, an electrode catalyst 1A of this invention has catalyst particles 3a each being composed of a core part 4; a shell part 5a covering a part of the surface of the core part 4; and a shell part 5b covering an other part of the surface of the core part 4.

With regard to the catalyst particles 3a contained in the electrode catalyst 1A shown in FIG. 2, there is a part of the core part 4 that is neither covered by the shell part 5a nor covered by the shell part 5b. This part of the core part 4 composes a core part-exposed surface 4s.

That is, as shown in FIG. 2, so far as the effects of this invention can be achieved, the catalyst particles 3a contained in the electrode catalyst 1A may also be in a state where the surface of the core part 4 is partially exposed (e.g. a state where 4s as a part of the surface of the core part 4 shown in FIG. 2 is exposed).

In other words, as is the case with the electrode catalyst 1A shown in FIG. 2, the shell part 5a may be partially formed on a part of the surface of the core part 4, and the shell part 5b may then be partially formed on another part of the surface of the core part 4.

Figure 3:
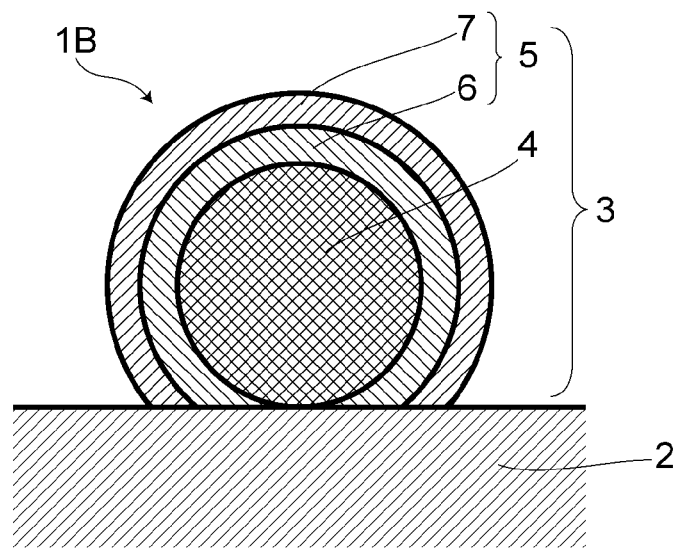
FIG. 3 is a schematic sectional view showing another example of the electrode catalyst (core-shell catalyst) of this invention.

FIG. 3 is a schematic cross-sectional view showing another preferable embodiment (electrode catalyst 1B) of the electrode catalyst (core-shell catalyst) of this invention.

As shown in FIG. 3, an electrode catalyst 1B of this invention has catalyst particles 3 each being composed of a core part 4; and a shell part 5 substantially covering the whole range of the surface of the core part 4.

The shell part 5 may have a two-layered structure composed of a first shell part 6 and a second shell part 7. That is, the catalyst particles 3 have a so-called "core-shell structure" comprised of the core part 4; and the shell part 5 (first shell part 6 and second shell part 7) formed on the core part 4.

The electrode catalyst 1B has a structure where the catalyst particles 3 are supported on the support 2, having the core part 4 serving as a core (core portion); and the whole range of the surface of the core part 4 is substantially covered by the shell part 5 composed of the first shell part 6 and the second shell part 7.

Here, the constituent element (chemical composition) of the core part 4, the constituent element (chemical composition) of the first shell part 6 and the constituent element (chemical composition) of the second shell part 7 differ from one another in composition.

Moreover, the shell part 5 included in the electrode catalyst 1B of this invention may further include another shell part in addition to the first shell part 6 and the second shell part 7.

In terms of more reliably achieving the effects of this invention, it is preferred that the electrode catalyst 1B be in a state where the whole range of the surface of the core part 4 is substantially covered by the shell part 5, as shown in FIG. 3.

Figure 4:
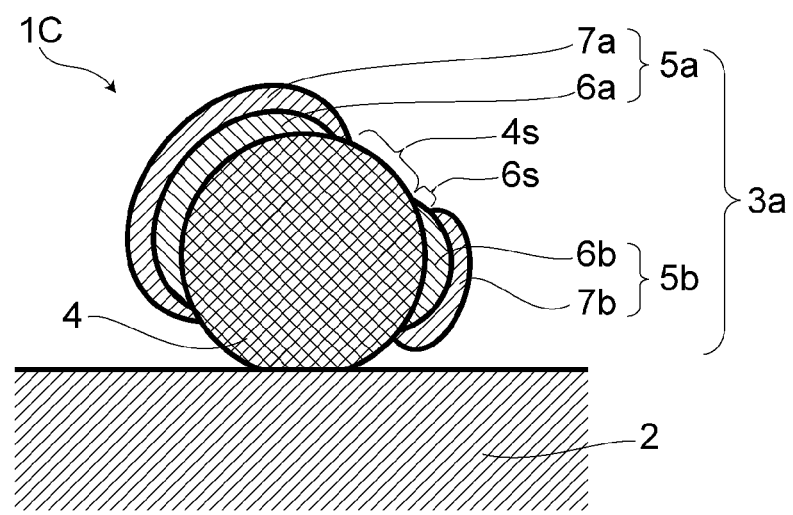
FIG. 4 is a schematic sectional view showing another example of the electrode catalyst (core-shell catalyst) of this invention.

FIG. 4 is a schematic cross-sectional view showing another preferable embodiment (electrode catalyst 1C) of the electrode catalyst (core-shell catalyst) of this invention.

As shown in FIG. 4, an electrode catalyst 1C of this invention has catalyst particles 3a each being composed of a core part 4; a shell part 5a covering a part of the surface of the core part 4; and a shell part 5b covering another part of the surface of the core part 4.

The shell part 5a may have a two-layered structure composed of a first shell part 6a and a second shell part 7a.

Further, the shell part 5b may have a two-layered structure composed of a first shell part 6b and a second shell part 7b.

That is, the catalyst particles 3a have a so-called "core-shell structure" including the core part 4; the shell part 5a (first shell part 6a and second shell part 7a) formed on the core part 4; and the shell part 5b (first shell part 6b and second shell part 7b) formed on the core part 4.

With regard to the shell part 5b composing the catalyst particle 3a shown in FIG. 4, there is a part of the first shell part 6b that is not covered by the second shell part 7b. The part of the first shell part 6b that is not covered by the second shell part 7b composes a first shell part-exposed surface 6s.

With regard to the shell part 5a composing the catalyst particle 3a shown in FIG. 4, it is preferred that the whole range of the first shell part 6a be substantially covered by the second shell part 7a.

Further, as shown in FIG. 4 and with regard to the shell part 5b composing each catalyst particle 3a, also permissible is a state where a part of the surface of the first shell part 6b is covered, and the surface of the first shell part 6b is thus partially exposed (e.g. a state shown in FIG. 4 where the part 6s of the surface of the first shell part 6b is exposed), so far as the effects of this invention can be achieved.

Moreover, on the premise that the effects of this invention can be achieved, the electrode catalyst 1 may allow a "complex of the core part 4 and shell part 5 with the whole range of the surface of the core part 4 being substantially covered by the shell part 5" and a "complex of the core part 4 and shell part 5 with the surface of the core part 4 being partially covered by the shell part 5" to coexist on the support 2 in a mixed manner.

Specifically, the electrode catalyst of this invention may be in a state where the electrode catalysts 1 and 1A shown in FIGS. 1 and 2 and the electrode catalysts 1B and 1C shown in FIGS. 3 and 4 coexist in a mixed manner, provided the effects of this invention can be achieved.

Further, the electrode catalyst of this invention may allow the shell part 5a and the shell part 5b to coexist in a mixed manner with respect to an identical core part 4, as shown in FIG. 4, so far as the effects of this invention can be achieved.

Furthermore, so far as the effects of this invention can be achieved, the electrode catalyst of this invention may allow only the shell part 5a to exist with respect to an identical core part 4 or only the shell part 5b to exist with respect to an identical core part 4 (none of these states are shown in the drawings).

Furthermore, so far as the effects of this invention can be achieved, the electrode catalyst 1 may also be in a state where "particles only composed of the core parts 4 that are not covered by the shell parts 5" are supported on the support 2, in addition to at least one kind of the electrode catalysts 1, 1A, 1B and 1C (not shown).

Furthermore, on the premise that the effects of this invention can be achieved, the electrode catalyst 1 may also be in a state where "particles only composed of the constituent element of the shell part 5" are supported on the support 2 without being in contact with the core parts 4, in addition to at least one kind of the electrode catalysts 1, 1A, 1B and 1C (not shown).

Furthermore, on the premise that the effects of this invention can be achieved, the electrode catalyst 1 may also be in a state where "particles only composed of the core parts 4 that are not covered by the shell parts 5" and "particles only composed of the constituent element of the shell part 5" are individually and independently supported on the support 2, in addition to at least one kind of the electrode catalysts 1, 1A, 1B and 1C.

It is preferred that the core part 4 have an average particle diameter of 2 to 40 nm, more preferably 4 to 20 nm, particularly preferably 5 to 15 nm.

As for the thickness of the shell part 5 (thickness from the surface in contact with the core part 4 to the outer surface of the shell part 5), a preferable range thereof is to be appropriately determined based on the design concept(s) of the electrode catalyst.

For example, when the amount of the metal element (e.g. platinum) used to compose the shell part 5 is intended to be minimized, a layer composed of one atom (one atomic layer) is preferred. In this case, when there is only one kind of metal element composing the shell part 5, it is preferred that the thickness of the shell part 5 be twice as large as the diameter of one atom of such metal element (in spherical approximation). Further, when there are not fewer than two kinds of metal elements composing the shell part 5, it is preferred that the thickness of the shell part 5 be that of a layer of one atom (one atomic layer formed with two or more kinds of atoms being apposed on the surface of the core part 4).

Further, for example, when attempting to improve a durability by employing a shell part 5 of a larger thickness, it is preferred that such thickness be 1 to 10 nm, more preferably 2 to 5 nm.

When the shell part 5 has the two-layered structure composed of the first shell part 6 and the second shell part 7, preferable ranges of the thicknesses of the first shell part 6 and second shell part 7 are appropriately determined based on the design concept(s) of the electrode catalyst of this invention.

For example, when the amount of a noble metal such as platinum (Pt) as a metal element contained in the second shell part 7 is intended to be minimized, it is preferred that the second shell part 7 be a layer composed of one atom (one atomic layer). In this case, when there is only one kind of metal element composing the second shell part 7, it is preferred that the thickness of the second shell part 7 be approximately twice as large as the diameter of one atom of such metal element (provided that an atom is considered as a sphere).

Further, when there are not fewer than two kinds of metal elements contained in the second shell part 7, it is preferred that the second shell part 7 have a thickness equivalent to that of a layer composed of not fewer than one kind of atom (one atomic layer formed with two or more kinds of atoms being apposed in the surface direction of the core part 4). For example, when attempting to improve the durability of the electrode catalyst by employing a second shell part 7 of a larger thickness, it is preferred that the thickness of the second shell part 7 be 1.0 to 5.0 nm. If the durability of the electrode catalyst is to be further improved, it is preferred that the thickness of the second shell part 7 be 2.0 to 10.0 nm.

Here, in this invention, "average particle diameter" refers to an average value of the diameters of an arbitrary number of particles as particle groups that are observed through electron micrographs.

There are no particular restrictions on the support 2, as long as such support 2 is capable of supporting the catalyst particles 3 as the complexes composed of the core parts 4 and the shell parts 5, and has a large surface area.

Moreover, it is preferred that the support 2 be that exhibiting a favorable dispersibility and a superior electrical conductivity in a composition used to form a gas diffusion electrode having the electrode catalyst 1.

The support 2 may be appropriately selected from carbon-based materials such as glassy carbon (GC), fine carbon, carbon black, black lead, carbon fiber, activated carbon, ground product of activated carbon, carbon nanofiber and carbon nanotube; and glass-based or ceramic-based materials such as oxides.

Among these materials, carbon-based materials are preferred in terms of their adsorptivities with respect to the core part 4 and in terms of a BET specific surface area of the support 2.

Further, as a carbon-based material, an electrically conductive carbon is preferred. Particularly, an electrically conductive carbon black is preferred as an electrically conductive carbon. Examples of such electrically conductive carbon black include products by the names of "Ketjenblack EC300 J," "Ketjenblack EC600" and "Carbon EPC" (produced by Lion Corporation).

There are no particular restrictions on the component of the core part 4, as long as the component is capable of being covered by the shell part 5.

When the shell part 5 employs a single-layered structure as are the cases with the electrode catalysts 1 and 1A that are shown in FIGS. 1 and 2 instead of the two-layered structure, from the viewpoint of relatively easily obtaining a superior catalytic activity, it is preferable that the core part 4 include a noble metal(s) as a main component(s). The core part 4 composing the catalyst particles 3 and 3a of the electrode catalysts 1 and 1A, contains at least one kind of metal selected from the group consisting of palladium (Pd), a palladium (Pd) alloy, a platinum (Pt) alloy, gold (Au), nickel (Ni) and a nickel (Ni) alloy.

There are no particular restrictions on a palladium (Pd) alloy, as long as the alloy is to be obtained by combining palladium (Pd) with another metal capable of forming an alloy when combined with palladium (Pd). For example, such palladium (Pd) alloy may be a two-component palladium (Pd) alloy obtained by combining palladium (Pd) with another metal; or a three or more-component palladium (Pd) alloy obtained by combining palladium (Pd) with not fewer than two kinds of other metals. Specifically, examples of such two-component palladium (Pd) alloy include gold palladium (PdAu), silver palladium (PdAg) and copper palladium (PdCu). One example of a three-component palladium (Pd) alloy is gold-silver-palladium (PdAuAg).

There are no particular restrictions on a platinum (Pt) alloy, as long as the alloy is to be obtained by combining platinum (Pt) with another metal capable of forming an alloy when combined with platinum (Pt). For example, such platinum (Pt) alloy may be a two-component platinum (Pt) alloy obtained by combining platinum (Pt) with another metal; or a three or more-component platinum (Pt) alloy obtained by combining platinum (Pt) with not fewer than two kinds of other metals. Specifically, examples of such two-component platinum (Pt) alloy include nickel platinum (PtNi) and cobalt platinum (PtCo).

There are no particular restrictions on a nickel (Ni) alloy, as long as the alloy is to be obtained by combining nickel (Ni) with another metal capable of forming an alloy when combined with nickel (Ni). For example, such nickel (Ni) alloy may be a two-component nickel (Ni) alloy obtained by combining nickel (Ni) with another metal; or a three or more-component nickel (Ni) alloy obtained by combining nickel (Ni) with not fewer than two kinds of other metals. Specifically, one example of such two-component nickel (Ni) alloy is tungsten nickel (NiW).

The shell part 5 contains at least one kind of metal selected from platinum (Pt) and a platinum (Pt) alloy. There are no particular restrictions on a platinum (Pt) alloy, as long as the alloy is to be obtained by combining platinum (Pt) with an other metal capable of forming an alloy when combined with platinum (Pt). For example, such platinum (Pt) alloy may be a two-component platinum (Pt) alloy obtained by combining platinum (Pt) with an other metal; or a three or more-component platinum (Pt) alloy obtained by combining platinum (Pt) with not fewer than two kinds of other metals. Specifically, examples of such two-component platinum (Pt) alloy include nickel platinum (PtNi), cobalt platinum (PtCo), platinum ruthenium (PtRu), platinum molybdenum (PtMo) and platinum titanium (PtTi). Particularly, in order for the shell part 5 to have a poisoning resistance against carbon monoxide, it is preferred that a platinum ruthenium (PtRu) alloy be used.

Further, when the shell part 5 employs the single-layered structure as are the cases with the electrode catalysts 1 and 1A that are shown in FIGS. 1 and 2 instead of the two-layered structure, from the perspective of reducing the cost for producing the electrode catalyst 1, it is preferred that the core part 4 include a metal element(s) other than noble metals as a main component(s) (the amount of the main component(s) is preferably not less than 60% by weight, more preferably not less than 70% by weight, further preferably not less than 80% by weight of the core part 4).

Specifically, when the shell part 5 employs the single-layered structure, it is preferred that the core part 4 contain, as a main component(s) thereof, a metal(s) including a metal element(s) other than noble metals, a metal nitride of such metal, a metal carbide of such metal, a metal oxide of such metal, an alloy containing such metal (a solid solution containing such metal and an intermetallic compound containing such metal), and/or a mixture of such metal(s) and such metal compound (s) (the amount of the main component(s) is preferably not less than 60% by weight, more preferably not less than 70% by weight, and further preferably not less than 80% by weight of the core part 4). In this case, it is preferred that the metal elements other than noble metals be metal elements other than Pt, Pd, Au, Ag, Rh, Ir, Ru and Os.

Further, in this case, it is preferred that the metal nitride be at least one kind selected from the group of Ti nitride, Zr nitride, Ta nitride, Nb nitride and W nitride.

Moreover, in this case, it is preferred that the metal carbide be at least one kind selected from the group of Ti carbide, Zr carbide, Ta carbide, Nb carbide and W carbide.

Furthermore, in this case, it is preferred that the metal oxide be at least one kind selected from the group of Ti oxide, Zr oxide, Ta oxide, Nb oxide and W oxide.

Further, as the electrode catalysts 1B and 1C illustrated in FIGS. 3 and 4, when the shell part 5 employs the two-layered structure composed of the first shell part 6 and the second shell part 7, it is preferred, especially from the perspective of reducing the cost for producing the electrode catalyst 1, that the core part 4 contain a metal element(s) other than noble metals as a main component(s) (the amount of main component is preferably not less than 60% by weight, more preferably not less than 70% by weight, further preferably not less than 80% by weight of the core part 4).

Specifically, when the shell part 5 employs the two-layered structure, it is preferred that the core part 4 contain, as a main component(s) thereof, a metal(s) including a metal element(s) other than noble metals, a metal nitride of such metal, a metal carbide of such metal, a metal oxide of such metal, an alloy containing such metal (a solid solution containing such metal and an intermetallic compound containing such metal), and/or a mixture of such metal(s) and such metal compound (the amount of the main component(s) is preferably not less than 60% by weight, more preferably not less than 70% by weight, and further preferably not less than 80% by weight of the core part 4). In this case, it is preferred that the metal elements other than noble metals be metal elements other than Pt, Pd, Au, Ag, Rh, Ir, Ru and Os.

Further, in this case, it is preferred that the metal nitride be at least one kind selected from the group of Ti nitride, Zr nitride, Ta nitride, Nb nitride and W nitride.

Moreover, in this case, it is preferred that the metal carbide be at least one kind selected from the group of Ti carbide, Zr carbide, Ta carbide, Nb carbide and W carbide.

Furthermore, in this case, it is preferred that the metal oxide be at least one kind selected from the group of Ti oxide, Zr oxide, Ta oxide, Nb oxide and W oxide.

A supported amount of the platinum (Pt) contained in the shell part 5 is 5 to 30% by weight, preferably 8 to 25% by weight with respect to the weight of the electrode catalyst 1. It is preferred that the amount of the platinum (Pt) supported be not smaller than 5% by weight, because the electrode catalyst can fully exert its catalytic activity in such case. It is also preferred that the amount of the platinum (Pt) supported be not larger than 30% by weight, because the amount of platinum (Pt) used is thus reduced in such case, which is favorable in terms of production cost.

In the case where the shell part 5 has the two-layered structure composed of the first shell part 6 and the second shell part 7, it is preferred that the first shell part 6 contain at least one kind of metal selected from the group consisting of palladium (Pd), a palladium (Pd) alloy, a platinum (Pt) alloy, gold (Au), nickel (Ni) and a nickel (Ni) alloy, and it is more preferred that the first shell part 6 contain elemental palladium (Pd).

From the perspective of further improving the catalytic activities of the electrode catalysts 1B and 1C and more easily obtaining the same, it is preferred that the first shell part 6 be mainly composed of palladium (Pd) simple substance (not less than 50 wt %), and it is more preferred that such first shell part 6 be only composed of palladium (Pd) simple substance.

It is preferred that the second shell part 7 contain at least one kind of metal selected from platinum (Pt) and a platinum (Pt) alloy, and it is more preferred that such shell part 7 contain platinum (Pt) simple substance.

From the perspective of further improving the catalytic activities of the electrode catalysts 1B and 1C and more easily obtaining the same, it is preferred that the second shell part 7 be mainly composed of platinum (Pt) simple substance (not less than 50 wt %), and it is more preferred that such second shell part 7 be only composed of platinum (Pt) simple substance.

Concentration of bromine (Br) species and concentration of chlorine (Cl) species The electrode catalyst 1 exhibits a bromine (Br) species concentration of not greater than 400 ppm (0 to 400 ppm), preferably not greater than 300 ppm (0 to 300 ppm), more preferably not greater than 200 ppm (0 to 200 ppm) when measured through X-ray fluorescence (XRF) spectroscopy. Further, the electrode catalyst 1 satisfies the abovementioned conditions of the bromine (Br) species concentration, and a chlorine (Cl) species concentration of not greater than 900 ppm (0 to 900 ppm) when measured through the same analytical method. The chlorine (Cl) species concentration is preferably less than 900 ppm (not less than 0 ppm and not greater than 900 ppm), more preferably not greater than 800 ppm (0 to 800 ppm), further preferably not greater than 600 ppm (0 to 600 ppm).

The electrode catalyst 1 is capable of fully exerting its catalytic activity as an electrode catalyst by concurrently fulfilling the abovementioned conditions of the chloride (Cl) species concentration and the bromine (Br) species concentration.

Here, the bromine (Br) species concentration and the chlorine (Cl) species concentration are measured through X-ray fluorescence (XRF) spectroscopy. A value obtained by measuring the bromine (Br) species contained in the electrode catalyst through X-ray fluorescence (XRF) spectroscopy is the bromine (Br) species concentration. Similarly, a value obtained by measuring the chlorine (Cl) species contained in the electrode catalyst through X-ray fluorescence (XRF) spectroscopy is the chlorine (Cl) species concentration.

Here, the bromine (Br) species concentration and the chlorine (Cl) species concentration are respectively the concentrations of the bromine atoms and chlorine atoms in terms of the bromine and chlorine elements contained in the electrode catalyst.

X-ray fluorescence (XRF) spectroscopy is a method where a specimen containing a particular element A is irradiated with a primary X-ray to generate a fluorescent X-ray of such element A, followed by measuring the intensity of such fluorescent X-ray of the element A such that quantitative analysis of the captioned element A contained in the specimen can be performed. When performing quantitative analysis through X-ray fluorescence (XRF) spectroscopy, there may be employed the fundamental parameter method (FP method) used in theoretical operation.

The FP method applies the idea that if the compositions and kinds of the elements contained in a specimen are all known, the fluorescent X-ray (XRF) intensities thereof can be individually and theoretically calculated. In addition, the FP method allows there to be estimated a composition(s) corresponding to the fluorescent X-ray (XRF) of each element that is obtained by measuring the specimen.

X-ray fluorescence (XRF) spectroscopy is performed using general fluorescent X-ray (XRF) analyzers such as an energy dispersive fluorescent X-ray (XRF) analyzer, a scanning-type fluorescent X-ray (XRF) analyzer and a multi-element simultaneous-type fluorescent X-ray (XRF) analyzer. A fluorescent X-ray (XRF) analyzer is equipped with a software which makes it possible to perform experimental data processing regarding the correlation between the intensity of the fluorescent X-ray (XRF) of the element A and the concentration of the element A.

There are no particular restrictions on such software, as long as the software is that generally used to perform X-ray fluorescence (XRF) spectroscopy.

For example, there may be employed a software for use in a general fluorescent X-ray (XRF) analyzer adopting the FP method, such as an analysis software: "UniQuant 5." Here, one example of the abovementioned fluorescent X-ray (XRF) analyzer is a full-automatic wavelength dispersive fluorescent X-ray analyzer (product name: Axios by Spectris Co., Ltd.).

In order to achieve a bromine (Br) species concentration of not greater than 400 ppm when measured by the X-ray fluorescence (XRF) spectroscopy, it is required that a metal compound as a starting material of the electrode catalyst 1 and a reagent(s) used in each production step of the electrode catalyst 1 be carefully selected. Specifically, there may, for example, be used a metal compound that does not generate bromine (Br) species, as the metal compound serving as the starting material of the electrode catalyst 1. Further, there may, for example, be employed a compound(s) that do not contain bromine (Br) species, as the reagent(s) used in the production steps of the electrode catalyst 1.

In order to achieve a chlorine (Cl) species concentration of not greater than 900 ppm when measured by the abovementioned X-ray fluorescence (XRF) spectroscopy, it is required that a metal compound as a starting material of the electrode catalyst 1 and reagents used in production steps of the electrode catalyst be carefully selected. Specifically, there may, for example, be used a metal compound that does not generate chlorine (Cl) species, as the metal compound serving as the starting material of the electrode catalyst 1. Further, there may, for example, be employed compounds that do not contain chlorine (Cl) species, as the reagents used in the production steps of the electrode catalyst 1.

Further, chlorine (Cl) species can be reduced to equal to or less than 900 ppm by employing the chlorine reduction methods described later.

A production method of the electrode catalyst 1 includes a step of producing an electrode catalyst precursor; and a step of washing such catalyst precursor to meet the condition where the bromine (Br) species concentration measured by the X-ray fluorescence (XRF) spectroscopy is not greater than 400 ppm, and the chlorine (Cl) species concentration measured by the same method is 0 to 900 ppm.

The electrode catalyst precursor of the electrode catalyst 1 is produced by having the support 2 support the catalyst components (core part 4, shell part 5) of the electrode catalyst.

There are no particular restrictions on a production method of the electrode catalyst precursor as long as the method allows the catalyst components of the electrode catalyst 1 to be supported on the support 2.

Examples of the production method of the electrode catalyst precursor include an impregnation method where a solution containing the catalyst components of the electrode catalyst 1 is brought into contact with the support 2 to impregnate the support 2 with the catalyst components; a liquid phase reduction method where a reductant is put into a solution containing the catalyst components of the electrode catalyst 1; an electrochemical deposition method such as under-potential deposition (UPD); a chemical reduction method; a reductive deposition method using adsorption hydrogen; a surface leaching method of alloy catalyst; immersion plating; a displacement plating method; a sputtering method; and a vacuum evaporation method.

Concentration of bromine (Br) species and concentration of chlorine (Cl) speNext, the concentrations of the bromine (Br) species and chlorine (Cl) species of the electrode catalyst precursor are adjusted to meet the condition where the bromine (Br) species concentration measured by the X-ray fluorescence (XRF) spectroscopy is not greater than 400 ppm, and the chlorine (Cl) species concentration measured by the same method is 0 to 900 ppm. Specifically, there are employed the following chlorine reduction methods 1 to 3.

Chlorine reduction method 1First step: The first step is to prepare a first liquid with an electrode catalyst precursor (I) being dispersed in an ultrapure water. The first liquid is prepared by adding such electrode catalyst precursor (I) to the ultrapure water. Here, the electrode catalyst precursor (I) is produced using a material containing chlorine (Cl) species, and exhibits a chlorine (Cl) species concentration higher than a predetermined chlorine (Cl) species concentration when measured by the X-ray fluorescence (XRF) spectroscopy (e.g. an electrode catalyst precursor exhibiting a chlorine (Cl) species concentration value higher than 8,500 ppm or 7,600 ppm, provided that 8,500 ppm or 7,600 ppm is the predetermined chlorine (Cl) species concentration).

Second step: The second step is to prepare a second liquid with an electrode catalyst precursor (II) being dispersed in the ultrapure water. Specifically, the electrode catalyst precursor (I) contained in the first liquid is filtrated and washed using the ultrapure water, followed by repeatedly washing the same until a filtrate obtained after washing has exhibited an electric conductivity ρ that is not higher than a predetermined value when measured by a JIS-standard testing method (JIS K0552) (e.g. not higher than a value predetermined within a range of 10 to 100 μS/cm). In this way, there is obtained the electrode catalyst precursor (II) as well as the second liquid with such electrode catalyst precursor (II) being dispersed in the ultrapure water.

Chlorine reduction method 2First step: The first step is to retain a liquid containing an ultrapure water, a reductant and an electrode catalyst precursor under at least one temperature predetermined within a range of 20 to 90° C. for a predetermined retention time. Here, the electrode catalyst precursor is produced using a material containing chlorine (Cl) species, and exhibits a chlorine (Cl) species concentration higher than a predetermined chlorine (Cl) species concentration when measured by the X-ray fluorescence (XRF) spectroscopy (e.g. an electrode catalyst precursor exhibiting a chlorine (Cl) species concentration value higher than 8,500 ppm or 6,000 ppm, provided that 8,500 ppm or 6,000 ppm is the predetermined chlorine concentration).

Second step: The second step is to add the ultrapure water to the liquid obtained in the first step so as to prepare a first liquid where an electrode catalyst precursor (I) contained in the liquid obtained in the first step is dispersed in the ultrapure water.

Third step: The third step is to filtrate and wash the electrode catalyst precursor contained in the first liquid using the ultrapure water, followed by repeatedly washing the same until a filtrate obtained after washing has exhibited an electric conductivity ρ that is not higher than a predetermined first value when measured by a JIS-standard testing method (JIS K0552). In this way, there is now obtained a second liquid where dispersed in the ultrapure water is the electrode catalyst precursor contained in the liquid having an electric conductivity ρ that is not higher than the predetermined first value.

Fourth step: The fourth step is to dry the second liquid.

Chlorine reduction method 3First step: The first step is to retain a liquid containing an ultrapure water, a gas having hydrogen and an electrode catalyst precursor under at least one temperature predetermined within a range of 20 to 40° C. for a predetermined retention time. Here, the electrode catalyst precursor is produced using a material containing chlorine (Cl) species, and exhibits a chlorine (Cl) species concentration higher than a predetermined chlorine (Cl) species concentration when measured by the X-ray fluorescence (XRF) spectroscopy.

The "ultrapure water" used in the chlorine reduction methods 1 to 3 is a type of water exhibiting a specific resistance R of not lower than 3.0 MΩ·cm, such specific resistance R being represented by the following general formula (1) (i.e. an inverse number of the electric conductivity measured by the JIS-standard testing method (JIS K0552)). Further, it is preferred that the "ultrapure water" have a water quality equivalent to or clearer than "A3" as defined in JISK 0557 "Water used for industrial water and wastewater analysis."

[Formula 1]

$$R=1/\rho \quad (1)$$

In the above general formula (1), R represents the specific resistance, and ρ represents the electric conductivity measured by the JIS-standard testing method (JIS K0552).

There are no particular restrictions on the ultrapure water, as long as the water has an electric conductivity that satisfies the relationship represented by the general formula (1). Examples of such ultrapure water include an ultrapure water produced using an ultrapure water system from "Milli-Q series" (by Merck Ltd.); and an ultrapure water produced using an ultrapure water system from "Elix UV series" (by Nihon Millipore K.K.).

The chlorine (Cl) species contained in the electrode catalyst precursor can be reduced by performing any one of the chlorine reduction methods 1 to 3. Thus can be obtained an electrode catalyst 1 in which a bromine (Br) species concentration is adjusted to be not greater than 400 ppm, and a chlorine (Cl) species concentration is adjusted to be within the range of 0 to 900 ppm when measured by the X-ray fluorescence (XRF) spectroscopy.

X-ray fluorescence (XRF) spectroscopy The X-ray fluorescence (XRF) spectroscopy is, for example, performed in the following manner.

(1) Measurement Device
   Full-automatic wavelength dispersive fluorescent X-ray analyzer Axios (by Spectris Co., Ltd.)

(2) Measurement Condition
   Analysis software: "UniQuant 5" (Semi-quantitative analysis software employing FP (four peak method))
   XRF measurement chamber atmosphere: Helium (normal pressure)

(3) Measurement Procedure
(i) Placing a sample-containing sample container into an XRF sample chamber
(ii) Replacing an atmosphere in the XRF sample chamber with helium gas
(iii) Setting the measurement condition to "UQ5 application" as a condition required to use the analysis software "UniQuant 5" and configuring a mode where calculation is performed in a mode with the main component of the sample being "carbon (constituent element of support)" and with a sample analysis result-display format being "element," under a helium gas atmosphere (normal pressure)

Figure 5:
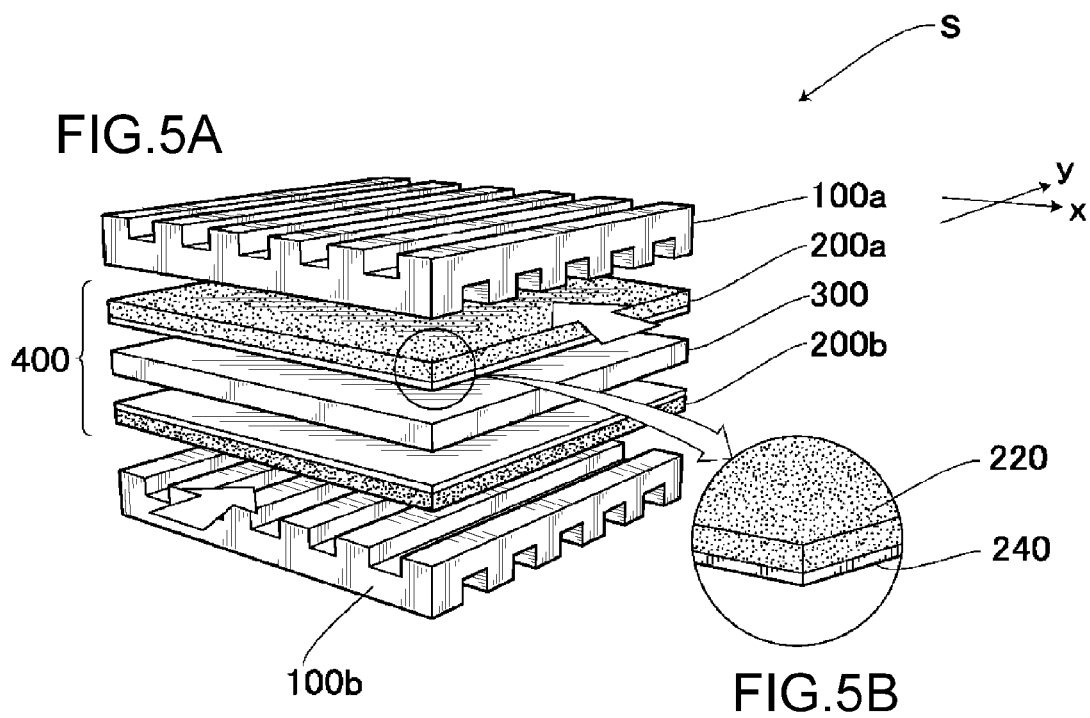
FIG. 5A is a schematic diagram showing an example of a fuel cell stack of this invention.
FIG. 5B is a magnified portion of FIG. 5A illustrating the gas diffusion layer and an electrode catalyst layer of the present invention.

FIGS. 5A and 5B are a schematic view showing preferable embodiments of a composition for forming gas diffusion electrode containing the electrode catalyst of this invention; a gas diffusion electrode produced using such composition for forming gas diffusion electrode; a membrane-electrode assembly (MEA) having such gas diffusion electrode; and a fuel cell stack having such membrane-electrode assembly (MEA).

As for a fuel cell stack S shown in FIG. 5A, each membrane-electrode assembly (MEA) 400 serves as a one-unit cell, and the fuel cell stack S is configured by stacking multiple layers of such one-unit cells.

Particularly, the fuel cell stack S has a membrane-electrode assembly (MEA) 400 that is equipped with an anode 200*a*, a cathode 200*b* and an electrolyte membrane 300 provided between these electrodes.

More particularly, the fuel cell stack S has a structure where the membrane-electrode assembly (MEA) 400 is sandwiched between a separator 100*a* and a separator 100*b*.

Described hereunder are the composition for forming gas diffusion electrode, a gas diffusion electrode 200*a*, a gas diffusion electrode 200*b* and the membrane-electrode assembly (MEA) 400, all of which serve as members of the fuel cell stack S containing the electrode catalyst of this invention.

The electrode catalyst 1 can be used as a so-called catalyst ink component and serve as the composition for forming gas diffusion electrode in this invention. One feature of the composition for forming gas diffusion electrode in this invention is that this composition contains the aforementioned electrode catalyst. The main components of the composition for forming gas diffusion electrode are the abovementioned electrode catalyst and an ionomer solution. The ionomer solution contains water, alcohol and a polyelectrolyte exhibiting a hydrogen ion conductivity.

A mixing ratio between water and alcohol in the ionomer solution can be any ratio, as long as it is the kind of ratio capable of endowing a viscosity suitable for applying the composition for forming gas diffusion electrode to the electrode. In general, it is preferred that an alcohol be contained in an amount of 0.1 to 50.0 parts by weight with respect to 100 parts by weight of water. Further, it is preferred that the alcohol contained in the ionomer solution be a monohydric alcohol or a polyhydric alcohol. Examples of a monohydric alcohol include methanol, ethanol, propanol and butanol. Examples of a polyhydric alcohol include dihydric alcohols or trihydric alcohols. As a dihydric alcohol, there can be listed, for example, ethylene glycol, diethylene glycol, tetraethylene glycol, propylene glycol, 1,3-butanediol and 1,4-butanediol. As a trihydric alcohol, there may be used glycerin, for example. Further, the alcohol contained in the ionomer solution may be either one kind of alcohol or a combination of two or more kinds of alcohols. Here, the ionomer solution may also be appropriately allowed to contain an additive(s) such as a surfactant, if necessary.

For the purpose of dispersing the electrode catalyst, the ionomer solution contains a hydrogen ion-conductive polyelectrolyte as a binder component for improving an adhesion to a gas diffusion layer as a part composing the gas diffusion electrode. Although there are no particular restrictions on the polyelectrolyte, examples of such polyelectrolyte include known perfluorocarbon resins having sulfonate groups and/or carboxylic acid groups. As an easily obtainable hydrogen ion-conductive polyelectrolyte, there can be listed, for example, Nafion (registered trademark of Du Pont), ACIPLEX (registered trademark of Asahi Kasei Chemical Corporation) and Flemion (registered trademark of ASAHI GLASS Co., Ltd).

The composition for forming gas diffusion electrode can be produced by mixing, crushing and stirring the electrode catalyst and the ionomer solution. The composition for forming gas diffusion electrode may be prepared using crushing and mixing machines such as a ball mill and/or an ultrasonic disperser. A crushing and stirring conditions at the time of operating a crushing and mixing machine can be appropriately determined in accordance with the mode of the composition for forming gas diffusion electrode.

It is required that the composition of each of the electrode catalyst, water, alcohol(s) and hydrogen ion-conductive polyelectrolyte that are contained in the composition for forming gas diffusion electrode be that capable of achieving a favorable dispersion state of the electrode catalyst, allowing the electrode catalyst to be distributed throughout an entire catalyst layer of the gas diffusion electrode and improving the power generation performance of the fuel cell.

Particularly, it is preferred that the polyelectrolyte, alcohol(s) and water be respectively contained in an amount of 0.1 to 2.0 parts by weight, an amount of 0.01 to 2.0 parts by weight and an amount of 2.0 to 20.0 parts by weight with respect to 1.0 parts by weight of the electrode catalyst. It is more preferred that the polyelectrolyte, alcohol(s) and water be respectively contained in an amount of 0.3 to 1.0 parts by weight, an amount of 0.1 to 2.0 parts by weight and an amount of 5.0 to 6.0 parts by weight with respect to 1.0 parts by weight of the electrode catalyst. It is preferred that the composition of each component be within the abovementioned ranges, because when the composition of each component is within these ranges, not only a coating film made of the composition for forming gas diffusion electrode will not be spread too extensively on the gas diffusion electrode at the time of forming the film, but the coating film formed of the composition for forming gas diffusion electrode is also allowed to have an appropriate and uniform thickness.

Here, the weight of the polyelectrolyte refers to a weight when it is dry i.e. a weight without a solvent in a polyelectrolyte solution, whereas the weight of water refers to a weight including water contained in the polyelectrolyte solution.

The gas diffusion electrode (200a, 200b) of this invention has a gas diffusion layer 220; and an electrode catalyst layer 240 laminated on at least one surface of the gas diffusion layer 220. The aforementioned electrode catalyst is contained in the electrode catalyst layer 240 equipped in the gas diffusion electrode (200a, 200b). The gas diffusion electrode 200 of this invention can be used as an anode and a cathode.

In FIG. 5A, the gas diffusion electrode 200 on the upper side is referred to as the anode 200a, whereas the gas diffusion electrode 200 on the lower side is referred to as the cathode 200b for the sake of convenience.

In the case of the anode 200a, the electrode catalyst layer 240 serves as a layer where a chemical reaction of dissociating a hydrogen gas sent from the gas diffusion layer 220 into hydrogen ions takes place due to the function of the electrode catalyst 1 contained in the electrode catalyst layer 240. Further, in the case of the cathode 200b, the electrode catalyst layer 240 serves as a layer where a chemical reaction of bonding air (oxygen gas) sent from the gas diffusion layer 220 and the hydrogen ions that have traveled from the anode through the electrolyte membrane takes place due to the function of the electrode catalyst 1 contained in the electrode catalyst layer 240.

The electrode catalyst layer 240 is formed using the abovementioned composition for forming gas diffusion electrode. It is preferred that the electrode catalyst layer 240 have a large surface area such that the reaction between the electrode catalyst 1 and the hydrogen gas or air (oxygen gas) sent from the diffusion layer 220 is allowed take place to the fullest extent. Moreover, it is preferred that the electrode catalyst layer 240 be formed in a manner such that the electrode catalyst layer 240 has a uniform thickness as a whole. Although the thickness of the electrode catalyst layer 240 can be appropriately adjusted and there are no restrictions on such thickness, it is preferred that the electrode catalyst layer 240 have a thickness of 2 to 200 μm.

The gas diffusion layer 220 equipped to the gas diffusion electrode 200 serves as a layer provided to diffuse to each of the corresponding electrode catalyst layers 240 the hydrogen gas introduced from outside the fuel cell stack S into gas flow passages that are formed between the separator 100a and the gas diffusion layer 220a; and the air (oxygen gas) introduced from outside the fuel cell stack S into gas passages that are formed between the separator 100b and the gas diffusion layer 220b. In addition, the gas diffusion layer 220 plays a role of supporting the electrode catalyst layer 240 to the gas diffusion electrode 200 so as to immobilize the electrode catalyst layer 240 to the surface of the gas diffusion electrode 220. The gas diffusion layer 220 also plays a role of improving the contact between the electrode catalyst 1 contained in the electrode catalyst layer 240 and the hydrogen gas as well as air (oxygen gas).

The gas diffusion layer 220 has a function of favorably passing the hydrogen gas or air (oxygen gas) supplied from the gas diffusion layer 220 and then allowing such hydrogen gas or air to arrive at the electrode catalyst layer 240. For this reason, it is preferred that the gas diffusion layer 220 have a water-repellent property such that a pore structure as a microstructure in the gas diffusion layer 220 will not be blocked by the electrode catalyst 1 and a water generated at the cathode 200b. Therefore, the gas diffusion layer 220 has a water repellent component such as polyethylene terephthalate (PTFE).

There are no particular restrictions on a material(s) that can be used in the gas diffusion layer 220. That is, there can be employed a material(s) known to be used in a gas diffusion layer of a fuel cell electrode. For example, there may be used a carbon paper; or a material made of a carbon paper as a main raw material and an auxiliary raw material applied to the carbon paper as the main raw material, such auxiliary raw material being composed of a carbon powder as an optional ingredient, an ion-exchange water also as an optional ingredient and a polyethylene terephthalate dispersion as a binder. The thickness of the gas diffusion layer can be appropriately determined based on, for example, the size of a cell used in a fuel cell. While there are no particular restrictions on the thickness of the gas diffusion layer, a thin gas diffusion layer is preferred for the purpose of ensuring a short diffusion distance of a reactant gas. Meanwhile, since it is required that the gas diffusion layer also exhibit a mechanical strength at the time of performing coating and during an assembly process, there is usually used a gas diffusion layer having a thickness of about 50 to 300 μm, for example.

As for the gas diffusion electrodes 200a and 200b, an intermediate layer (not shown) may be provided between the gas diffusion layer 220 and the electrode catalyst layer 240. In such case, each of the gas diffusion electrodes 200a and 200b has a three-layered structure composed of the gas diffusion layer, the intermediate layer and the catalyst layer.

A production method of the gas diffusion electrode is described hereunder.

The production method of the gas diffusion electrode includes a step of applying the composition for forming gas diffusion electrode to the gas diffusion layer 220; and a step of forming the electrode catalyst layer 240 by drying such gas diffusion layer 220 to which the composition for forming gas diffusion electrode has been applied. The composition for forming gas diffusion electrode contains the electrode catalyst 1 with the catalyst components supported on the support and the ionomer solution containing a hydrogen ion-conductive polyelectrolyte, water and an alcohol(s).

The important point when applying to the gas diffusion layer 220 the composition for forming gas diffusion electrode is that the composition for forming gas diffusion electrode is to be homogeneously applied to the gas diffusion layer 220. As a result of homogeneously applying the composition for forming gas diffusion electrode, there can be formed on the gas diffusion layer 220 a coating film that has a uniform thickness and is made of the composition for forming gas diffusion electrode. Although an application quantity of the composition for forming gas diffusion electrode can be appropriately determined based on a mode of usage of the fuel cell, it is preferred that the quantity be 0.1 to 0.5 (mg/cm$^2$) in terms of the amount of an active metal such as platinum contained in the electrode catalyst layer 240, from the perspective of a cell performance of a fuel cell having a gas diffusion electrode.

Next, after applying to the gas diffusion layer 220 the composition for forming gas diffusion electrode, the coating film of the composition for forming gas diffusion electrode that has been applied to the gas diffusion layer 220 is dried so as to form the electrode catalyst layer 240 on the gas diffusion layer 220. By heating the gas diffusion layer 220 on which the coating film of the composition for forming gas diffusion electrode has been formed, the water and alcohol(s) in the ionomer solution contained in the composition for forming gas diffusion electrode will be evaporated and thus disappear from the composition for forming gas diffusion electrode. As a result, in the step of applying the composition for forming gas diffusion electrode, the coating film of the composition for forming gas diffusion electrode that is formed on the gas diffusion layer 220 becomes the electrode catalyst layer 240 containing the electrode catalyst and polyelectrolyte.

The membrane-electrode assembly 400 of this invention (Membrane Electrode Assembly, abbreviated as MEA hereunder) has the anode 200a and cathode 200b which serve as the gas diffusion electrodes 200 using the electrode catalyst 1; and the electrolyte 300 dividing these electrodes. The membrane-electrode assembly (MEA) 400 can be produced by stacking the anode 200a, the electrolyte 300 and the cathode 200b in an order of anode 200a, electrolyte 300 and cathode 200b, and then pressure-bonding the same.

As for the fuel cell stack S of this invention, the one-unit cell (single cell) is established with the separator 100a (anode side) being attached to an outer side of the anode 200a of the membrane-electrode assembly (MEA) 400 obtained, and with the separator 100b (cathode side) being attached to an outer side of the cathode 200b of the membrane-electrode assembly (MEA) 400, respectively. Further, the fuel cell stack S is obtained by integrating such one-unit cells (single cells). Furthermore, a fuel cell system is completed by attaching a peripheral device(s) to the fuel cell stack S and assembling the same.

This invention is described in greater detail hereunder with reference to working examples. However, this invention is not limited to the following working examples.

Here, the inventors of this invention confirmed that iodine (I) species was not detected from the catalysts of the working and comparative examples, when employing the X-ray fluorescence (XRF) spectroscopy.

Further, unless otherwise noted in the description of each step of the following production method, these steps were carried out under a room temperature and in the air.

Working Example 1

The electrode catalyst of this invention was produced through the following process. The raw materials of the electrode catalyst that were used in the working examples are as follows.

Carbon black powder: product name "Ketjen Black EC300" (by Ketjen Black International Co.)
Sodium tetrachloropalladate (II)
Palladium nitrate
Potassium chloroplatinate As a support of the electrode catalyst, there was used a carbon black powder which was dispersed in a water to prepare a dispersion liquid of 5.0 g/L. An aqueous solution of sodium tetrachloropalladate (II) (concentration 20% by mass) of 5 mL was then delivered by drops into and mixed with such dispersion liquid. An aqueous solution of sodium formate (100 g/L) of 100 mL was further delivered by drops into a dispersion liquid thus obtained, followed by taking the insoluble components through filtering and then washing the taken insoluble components with a pure water. After performing drying, there was then obtained a palladium (core)-supported carbon with palladium being supported on carbon black.

An aqueous solution of copper sulfate of 50 mM was poured into a three-electrode electrolytic cell. A reasonable amount of the palladium-supported carbon prepared above was then added to such three-electrode electrolytic cell, followed by stirring the same and then allowing the three-electrode electrolytic cell to stand still. 450 mV (pair reversible hydrogen electrode) was applied to the working electrode in a resting state such that copper (Cu) could uniformly coat the palladium of the palladium-supported carbon. This is defined as a copper-palladium supported carbon.

An aqueous solution of potassium chloroplatinic acid was delivered by drops into the solution containing the copper-palladium supported carbon with palladium being coated by copper, the aqueous solution of potassium chloroplatinic acid containing platinum (Pt) in an amount two-fold equivalent of the coating copper in terms of substance amount ratio. In this way, the copper (Cu) of the copper-palladium supported carbon was replaced with platinum (Pt).

After filtering a powder of the particles of such platinum palladium-supported carbon obtained by replacing the copper (Cu) of the copper-palladium supported carbon with platinum (Pt), without performing drying, an ultrapure water was used to wash the same in a wet state due to a filtrate, followed by drying the same at a temperature of 70° C. Thus, there was obtained an electrode catalyst precursor 1 {platinum (Pt)-palladium (Pd) supported carbon (core part: palladium, shell part: platinum)}, to be employed as a raw material of the electrode catalyst of this invention.

The electrode catalyst precursor 1 was soaked in an aqueous solution of sodium formate (0.0028M), and retained at a room temperature for a predetermined period of time. Then, the electrode catalyst precursor 1 in the aqueous solution of sodium formate was filtered and washed with ultrapure water. The filtering and washing with ultrapure water were repeated by a predetermined number of times. Next, the electrode catalyst washed with the ultrapure water, was dried at a temperature of 70° C. In this way, the electrode catalyst of the working example 1, having the loading amounts of platinum (Pt) and palladium (Pd) and the concentrations of chlorine (Cl) species and bromine (Br) species shown in Table 1, was obtained.

The loading amounts (% by weight) of platinum (Pt) and palladium (Pd) of the electrode catalyst of the working example 1 thus obtained, were measured by the following method. The electrode catalyst of the working example 1 was soaked in an aqua regia to dissolve the metal. Then, carbon as an insoluble component was removed from the aqua regia. Next, the aqua regina from which the carbon had been removed was analyzed by ICP analysis.

The results of ICP analysis showed that the loading amounts of platinum and palladium were respectively 23.8% by mass and 21.9% by mass.

Working Examples 2 to 3

In a similar manner to the working example 1 except that the time period of soaking the electrode catalyst precursor 1 in the aqueous solution of sodium formate (0.0028M) and the number of times of filtering and washing with ultrapure water were changed, there were prepared electrode catalysts of the working examples 2 to 3, having the loading amounts of platinum (Pt) and palladium (Pd) and the concentrations of chlorine (Cl) species and bromine (Br) species shown in Table 1.

The obtained electrode catalysts of the working examples 2 to 3 were analyzed by ICP analysis in a similar manner to the working example 1 to thereby measure the loading amounts of platinum and palladium.

Working Examples 4 to 5

Except that the concentration of the aqueous solution of sodium formate in which the electrode catalyst precursor 1 was soaked; the time period for soaking the same in the aqueous solution; and the number of times of filtering and washing with ultrapure water were changed, there were prepared, in a similar manner to the working example 1, electrode catalysts of the working examples 4 to 5, having the loading amounts of platinum (Pt) and palladium (Pd) and the concentrations of chlorine (Cl) species and bromine (Br) species shown in Table 1. It is to be noted that the concentration of the aqueous solution of sodium formate used in the working example 4 is 0.0025M and the one used in the working example 5 is 0.0040M.

Working Example 6

An electrode catalyst precursor 2 having different loading amounts of platinum (Pt) and palladium (Pd) was employed instead of the electrode catalyst precursor 1 used in the working example 1. This electrode catalyst precursor 2 was produced in a similar manner as the electrode catalyst precursor 1 until the washing and drying step of the working example 1, in which after the powder of the particles of the platinum palladium-supported carbon was filtered, the filtered powder of the particles of the platinum palladium-supported carbon being in a wet state with a filtrate, was washed with ultrapure water, and dried at a temperature of 70° C.

Except that when the electrode catalyst precursor 2 was processed with the aqueous solution of sodium formate, the concentration of the aqueous solution of sodium formate was rendered to be 0.010M, and the period of time for soaking the same in the aqueous solution and the number of times of filtering and washing with ultrapure water were changed, there was prepared, in a similar manner to the working example 1, an electrode catalyst of the working example 6, having the loading amounts of platinum (Pt) and palladium (Pd) and the concentrations of chlorine (Cl) species and bromine (Br) species shown in Table 1.

Further, ICP analysis was performed in a similar manner to the working example 1 to thereby measure the loading amounts of platinum and palladium.

Working Example 7

An electrode catalyst precursor 3 having different loading amounts of platinum and palladium, was employed instead of the electrode catalyst precursor 1 used in the working example 1. This electrode catalyst precursor 3 was produced in a similar manner to the production step of the electrode catalyst precursor 1 until the washing and drying step of the working example 1, in which after the powder of the particles of the platinum palladium-supported carbon was filtered, the filtered powder of the particles of the platinum palladium-supported carbon being in a wet state with a filtrate, was washed with ultrapure water, and dried at a temperature of 70° C.

Then, the powder of the electrode catalyst precursor 3 was soaked in an aqueous solution of oxalic acid (0.3M) instead of the aqueous solution of sodium formate, and retained at a temperature of 90° C. for a predetermined period of time. Then, the powder soaked in the aqueous solution of oxalic acid was filtered and washed with ultrapure water. Next, the powder washed with ultrapure water, was dried at a temperature of 70° C. In this way, the electrode catalyst of the working example 7, having the loading amounts of platinum (Pt) and palladium (Pd) and the concentrations of chlorine (Cl) species and bromine (Br) species shown in Table 1, was obtained.

Further, ICP analysis was performed in a similar manner to the working example 1 to thereby measure the loading amounts of platinum and palladium.

Working Examples 8 to 9

An electrode catalyst precursor 4 having different loading amounts of platinum and palladium was employed instead of the electrode catalyst precursor 1 used in the working example 1. This electrode catalyst precursor 4 was produced in a similar manner to the production step of the electrode catalyst precursor 1 until the washing and drying step of the working example 1, in which after the powder of the particles of the platinum palladium-supported carbon was filtered, the filtered powder of the particles of the platinum palladium-supported carbon, being in a wet state with a filtrate, was washed with ultrapure water, and dried at a temperature of 70° C.

Except that when the electrode catalyst precursor 4 was processed with the aqueous solution of sodium formate, the concentration of the aqueous solution of sodium formate was rendered to be 0.010M, and the period of time for soaking the same in the aqueous solution and the number of times of filtering and washing with ultrapure water were changed, there were prepared, in a similar manner to the working example 1, electrode catalysts of the working examples 8 to 9, having the loading amounts of platinum (Pt) and palladium (Pd) and the concentrations of chlorine (Cl) species and bromine (Br) species shown in Table 1.

Further, ICP analysis was performed in a similar manner to the working example 1 to measure the loading amounts of platinum and palladium.

Comparative Example 1

The electrode catalyst precursor 1 used in the working example 1 was used as it was, without filtering and washing the same by an aqueous solution of sodium formate or the like.

Comparative Example 2

An electrode catalyst precursor 5 having different loading amounts of platinum and palladium was employed instead of the electrode catalyst precursor 1 used in the working example 1. This electrode catalyst precursor 5 was produced in a similar manner to the production step of the electrode catalyst precursor 1 until the washing and drying step of the working example 1, in which after the powder of the particles of the platinum palladium-supported carbon was filtered, the filtered powder being in a wet state with a filtrate, was washed with ultrapure water, and dried at a temperature of 70° C.

The electrode catalyst precursor 5 thus obtained was, without filtering and washing the same with an aqueous solution of sodium formate or the like, was used as it was, for an electrode catalyst of comparative example 2.

In this way, the electrode catalyst of the comparative example 2, having the loading amounts of platinum (Pt) and palladium (Pd) and the concentrations of chlorine (Cl) species and bromine (Br) species shown in Table 1, was obtained.

Further, ICP analysis was performed in a similar manner to the working example 1 to thereby measure the loading amounts of platinum and palladium.

Comparative Example 3

An electrode catalyst precursor 6 having different loading amounts of platinum and palladium was employed instead of the electrode catalyst precursor 1 used in the working example 1. This electrode catalyst precursor 6 was produced in a similar manner to the production step of the electrode catalyst precursor 1 until the washing and drying step of the working example 1, in which after the powder of the particles of the platinum palladium-supported carbon was filtered, the filtered powder being in a wet state with a filtrate, was washed with ultrapure water, and dried at a temperature of 70° C.

Subsequently, the obtained electrode catalyst precursor 6 was further soaked in an aqueous solution of sodium formate (0.01M), and retained at a temperature of 90° C. for a predetermined period of time. Then, the electrode catalyst in the aqueous solution of sodium formate was filtered and washed with ultrapure water.

In this way, the electrode catalyst of the comparative example 3, having the loading amounts of platinum (Pt) and palladium (Pd) and the concentrations of chlorine (Cl) species and bromine (Br) species shown in Table 1, was obtained.

Further, ICP analysis was performed in a similar manner to the working example 1 to thereby measure the loading amounts of platinum and palladium. Concentrations of bromine (Br) species and chlorine (Cl) species X-ray fluorescence (XRF) spectrometry was employed to measure the concentrations of the bromine (Br) species and chlorine (Cl) species of the electrode catalysts that were obtained in the working examples 1 to 9, and the comparative examples 1 to 3. The concentrations of the bromine species and chlorine species in the electrode catalysts were measured using the wavelength dispersive fluorescent X-ray analyzer Axios (by Spectris Co., Ltd.). Specifically, the measurement was carried out through the following procedure.

A measurement sample of the electrode catalyst was placed in a XRF sample container equipped in the wavelength dispersive fluorescent X-ray analyzer. The XRF sample container in which the measurement sample of the electrode catalyst had been placed was then put into an XRF sample chamber, followed by replacing an atmosphere in the XRF sample chamber with a helium gas. Later, fluorescent X-ray measurement was conducted under the helium gas atmosphere (normal pressure).

As a software, there was used "UniQuant5" which is an analytic software for use in wavelength dispersive fluorescent X-ray analyzer. A measurement condition(s) were set to "UQ5 application" in accordance with the analytic software "UniQuant5," where calculation is performed in a mode with the main component of the measurement sample of the electrode catalyst being "carbon (constituent element of electrode catalyst support)" and with a sample analysis result-display format being "element." Measurement results were analyzed using the analytic software "UniQuant5" such that the concentrations of bromine (Br) species and chlorine (Cl) species were able to be calculated. The measurement results are shown in Table 1.

The catalytic activities of the electrode catalysts produced in the working examples 1 to 9, and the comparative examples 1 to 3, were evaluated by a rotating disk electrode method (RDE method). The catalytic activities of the electrode catalysts were measured by the rotating disk electrode method (RDE method) in the following manner.

A powder of each of the electrode catalysts produced in the working examples 1 to 9 and the comparative examples 1 to 3 was taken by an amount of about 8.0 mg through measurement, and was put into a sample bottle together with an ultrapure water of 2.5 mL, followed by mixing the same while being placed under the influence of an ultrasonic irradiation, thus producing a slurry (suspension) of the electrode catalyst. Next, there was prepared a Nafion-ultrapure water solution by mixing an ultrapure water of 10.0 mL and a 10% by weight Nafion (registered trademark) dispersion aqueous solution (product name "DE1020CS" by Wako Chemical Ltd.) of 20 μL in a different container. The Nafion-ultrapure water solution of 2.5 mL was slowly poured into the sample bottle containing the slurry (suspension) of the electrode catalyst, followed by thoroughly stirring the same at a room temperature for 15 min while under the influence of an ultrasonic irradiation, thus obtaining a composition for forming gas diffusion electrode.

Figure 6:
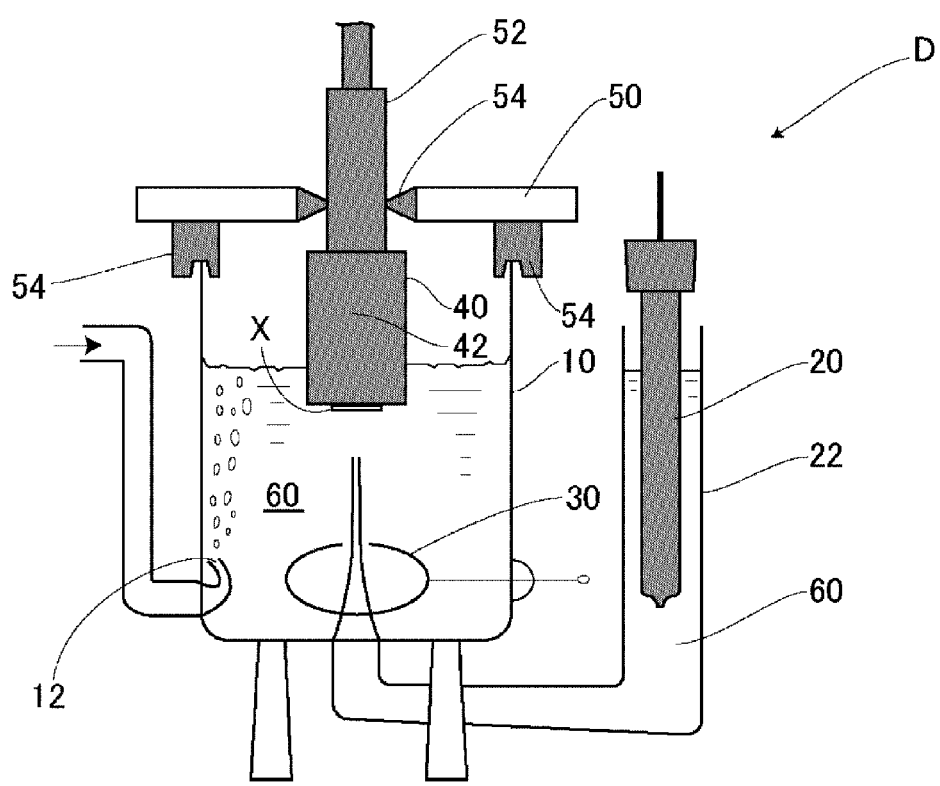
FIG. 6 is a schematic diagram showing a schematic configuration of a rotating disk electrode measuring device equipped with a rotating disc electrode used in a working example.

FIG. 6 is a schematic diagram showing a schematic configuration of a rotating disk electrode measuring device D used in the rotating disk electrode method (RDE method).

As shown in FIG. 6, the rotating disk electrode measuring device D mainly includes a measuring device cell 10, a reference electrode (RE) 20, a counter electrode (CE) 30, a rotating disk electrode 40 and an electrolyte solution 60.

An electrode catalyst layer X was formed on the surface of the rotating disk electrode 40 equipped to the rotating disk electrode measuring device D. Further, the catalyst of the electrode catalyst layer X was evaluated by the rotating disk electrode method.

Particularly, there was used a rotating disk electrode measuring device D (model HSV110 by Hokuto Denko Corp.) employing $HClO_4$ of 0.1M as the electrolyte 60, an Ag/AgCl saturated electrode as the reference electrode (RE) 20 and a Pt mesh with Pt black as the counter electrode (CE) 30.

A method for forming the electrode catalyst layer X on the surface of the rotating disk electrode 40 is described hereunder.

The composition for forming gas diffusion electrode that had been produced above was taken by an amount of 10 μL, and was delivered by drops onto the surface of the clean rotating disk electrode (made of glassy carbon, diameter 5.0 mmφ, area 19.6 mm²). Later, the composition for forming gas diffusion electrode was spread on the entire surface of the rotating disk electrode to form a uniform and given thickness, thereby forming on the surface of the rotating disk electrode a coating film made of the composition for forming gas diffusion electrode. The coating film made of the composition for forming gas diffusion electrode was dried under a temperature of 23° C. and a humidity of 50% RH for 2.5 hours, thus forming the electrode catalyst layer X on the surface of the rotating disk electrode 40.

Measurements by the rotating disk electrode method include performing cleaning inside the rotating disk electrode measuring device; an evaluation of electrochemical surface area (ECSA) prior to the measurement; an evaluation of electrochemical surface (ECSA) before and after an oxygen reduction (ORR) current measurement.

In the rotating disk electrode measuring device D, after soaking the rotating disk electrode 40 in $HClO_4$ electrolyte solution 60, the electrolyte solution 60 was purged with an argon gas for not shorter than 30 min. Then, potential scan was performed for 20 cycles under the condition where the scanning potential was set to be 85~1,085 mV vsRHE, and the scanning speed was set to be 50 mv/sec.

Then, potential scan was performed for three cycles under the condition where the scanning potential was set to be 50~1,085 mV vsRHE, and the scanning speed was set to be 20 mV/sec.

After purging the electrolyte solution 60 with an oxygen gas for not shorter than 15 minutes, a cyclic voltammogram (CV) measurement was performed for 10 cycles under the condition where the scanning potential was set to be 135 to 1,085 mV vsRHE, the scanning speed was set to be 10 mV/sec, and the rotation speed of the rotating disk electrode 40 was set to be 1,600 rpm. An electrical current value at a potential of 900 mV vsRHE was recorded. In addition, the rotation speed of the rotating disk electrode 40 was individually set to be 400 rpm, 625 rpm, 900 rpm, 1,225 rpm, 2,025 rpm, 2,500 rpm and 3,025 rpm, and an oxygen reduction (ORR) current measurement was carried out per each cycle. A current measurement value was defined as an oxygen reduction current value (i).

Finally, the cyclic voltammogram (CV) measurement was performed for three cycles under the condition where the scanning potential was set to be 50 to 1,085 mV vsRHE, and the scanning speed was set to be 20 mV/sec.

The catalytic activity of the electrode catalyst was calculated using a correction formula of mass transfer which is based on a Nernst diffusion-layer model as shown by the following general formula (2), with the aid of the oxygen reduction current value (i) obtained above and a limiting current value (iL) measured in the cyclic voltammogram (CV) measurement. The calculation results of the working examples 1 to 9 and the comparative examples 1 to 3 are shown in Table 1.

Formula 2

$$ik = \frac{iL \times i}{iL - i} \quad (2)$$

(In the general formula (2), i represents the oxygen reduction current (ORR current) measurement value, iL represents the limiting diffusion current measurement value, ik represents the catalytic activity.)

TABLE 1

| Working example | Pt/% by mass | Pd/% by mass | Bromine species concentration/ppm | Chlorine species concentration/ppm | ik/mA |
|---|---|---|---|---|---|
| Working example 1 | 23.8 | 21.9 | 200 | 900 | 2.51 |
| Working example 2 | 23.8 | 21.9 | 200 | 800 | 2.64 |
| Working example 3 | 23.8 | 21.9 | 200 | 600 | 2.85 |
| Working example 4 | 23.8 | 21.9 | 200 | 500 | 2.61 |
| Working example 5 | 23.8 | 21.9 | 200 | 100 | 2.83 |
| Working example 6 | 19.6 | 24.4 | 100 | 0 | 2.16 |
| Working example 7 | 23.5 | 21.5 | 100 | 900 | 2.20 |
| Working example 8 | 23.7 | 22.0 | 200 | 600 | 2.30 |
| Working example 9 | 23.7 | 22.0 | 200 | 500 | 2.30 |
| Comparative example 1 | 23.8 | 21.9 | 200 | 8400 | 1.90 |
| Comparative example 2 | 23.5 | 21.5 | 300 | 6100 | 1.68 |
| Comparative example 3 | 21.0 | 22.9 | 500 | 0 | 1.74 |

From Table 1, it became clear that, compared to the electrode catalysts obtained in the comparative examples 1 to 3, the electrode catalysts of the working examples 1 to 9 according to this invention were able to exhibit a significantly favorable catalytic activity.

The electrode catalyst of this invention is capable of demonstrating a sufficient catalytic performance due to the contents of chlorine (Cl) species and bromine (Br) species being reduced to the predetermined levels or lower. Accordingly, this invention is a type of electrode catalyst that can be used not only in fuel cells, fuel-cell vehicles and electrical equipment industries such as those related to cellular mobiles, but also in Ene farms, cogeneration systems or the like. Thus, the electrode catalyst of this invention shall make contributions to the energy industries and developments related to environmental technologies.

The invention claimed is:

1. An electrode catalyst having a core-shell structure comprising:
   a support;
   a core part formed on the support; and
   a shell part formed to cover at least a part of a surface of the core part,
   wherein the shell part includes a single-layered structure formed to cover at least a part of the surface of the core part, or a two-layered structure including a first shell part formed to cover at least a part of the surface of the core part, and a second shell part formed to cover at least a part of the surface of the first shell part,
   wherein in a case of the single-layered shell part, the shell part comprises platinum (Pt), and the core part comprises palladium (Pd), whilst in a case of the two-layered shell part, the first shell part comprises palladium (Pd), and the second shell part comprises platinum (Pt),
   wherein a concentration of bromine (Br) species measured by X-ray fluorescence (XRF) spectroscopy, is not greater than 400 ppm, and
   wherein a concentration of chlorine (Cl) species measured by X-ray fluorescence (XRF) spectroscopy, is less than 900 ppm.

2. The electrode catalyst according to claim 1, wherein the concentration of bromine (Br) species is not greater than 300 ppm.

3. The electrode catalyst according to claim 2, wherein the concentration of bromine (Br) species is not greater than 200 ppm.

4. The electrode catalyst according to claim 1, wherein the concentration of chlorine (Cl) species is equal to or greater than 0 ppm.

5. The electrode catalyst according to claim 1, wherein the concentration of chlorine (Cl) species is not less than 100 ppm.

6. The electrode catalyst according to claim 1, wherein, in a case of the two-layered shell part, the core part contains one or more metal elements other than noble metals as a main component(s).

7. A composition for forming a gas diffusion electrode, comprising the electrode catalyst according to claim 1.

8. A gas diffusion electrode comprising the electrode catalyst according to claim 1.

9. A membrane-electrode assembly (MEA) comprising the gas diffusion electrode according to claim 8.

10. A fuel cell stack comprising the membrane-electrode assembly (MEA) according to claim 9.

11. The electrode catalyst according to claim 2, wherein the concentration of chlorine (Cl) species is equal to or greater than 0 ppm.

12. The electrode catalyst according to claim 3, wherein the concentration of chlorine (Cl) species is equal to or greater than 0 ppm.

13. The electrode catalyst according to claim 2, wherein the concentration of chlorine (Cl) species not less than 100 ppm.

14. The electrode catalyst according to claim 3, wherein the concentration of chlorine (Cl) species not less than 100 ppm.

* * * * *